(12) United States Patent
Kim et al.

(10) Patent No.: US 11,896,718 B2
(45) Date of Patent: Feb. 13, 2024

(54) CORE TABLET COMPOSITE PREPARATION COMPRISING MOSAPRIDE AND RABEPRAZOLE

(71) Applicant: KOREA UNITED PHARM. INC., Seoul (KR)

(72) Inventors: Byung Jin Kim, Sejong (KR); Hee Yong Song, Daejeon (KR); Youn Woong Choi, Ansan (KR); Seong Yeob Kim, Sejong (KR)

(*) Notice: Subject to any disclaimer, the term of this patent is extended or adjusted under 35 U.S.C. 154(b) by 228 days.

(21) Appl. No.: 16/768,805

(22) PCT Filed: Nov. 26, 2018

(86) PCT No.: PCT/KR2018/014610
§ 371 (c)(1),
(2) Date: Jun. 1, 2020

(87) PCT Pub. No.: WO2019/117502
PCT Pub. Date: Jun. 20, 2019

(65) Prior Publication Data
US 2021/0177765 A1    Jun. 17, 2021

(30) Foreign Application Priority Data
Dec. 14, 2017 (KR) .................. 10-2017-0172473

(51) Int. Cl.
*A61K 9/20* (2006.01)
*A61K 9/24* (2006.01)
*A61K 9/28* (2006.01)
*A61K 31/4439* (2006.01)
*A61K 31/5375* (2006.01)

(52) U.S. Cl.
CPC ............ *A61K 9/209* (2013.01); *A61K 9/2018* (2013.01); *A61K 9/2027* (2013.01); *A61K 9/2054* (2013.01); *A61K 9/2806* (2013.01); *A61K 31/4439* (2013.01); *A61K 31/5375* (2013.01)

(58) Field of Classification Search
None
See application file for complete search history.

(56) References Cited

U.S. PATENT DOCUMENTS

| 6,132,771 A * | 10/2000 | Depui ............... A61K 45/06 424/490 |
| 11,000,481 B2 * | 5/2021 | Choi .................. A61P 1/00 |
| 2008/0161307 A1 | 7/2008 | Earnest et al. |
| 2010/0196471 A1 * | 8/2010 | Jain .................. A61K 9/209 514/212.07 |
| 2013/0017262 A1 | 1/2013 | Mullen et al. |

FOREIGN PATENT DOCUMENTS

| KR | 10-2017-0001545 A | 1/2017 | |
| KR | 10-2017-0001664 A | 1/2017 | |
| KR | 10-2017-0061219 A | 6/2017 | |
| WO | WO-2006011159 A2 * | 2/2006 | ......... A61K 31/4439 |
| WO | WO-2010038241 A2 * | 4/2010 | ......... A61K 31/4439 |
| WO | WO-2016209061 A * | 12/2016 | ........... A61K 31/416 |

OTHER PUBLICATIONS

International Search Report for PCT/KR2018/014610 dated May 15, 2019.

* cited by examiner

*Primary Examiner* — Susan T Tran (57) ABSTRACT

The present invention relates to a composite preparation in a core tablet form, composed of an inner core containing rabeprazole as an effective ingredient; an outer layer portion including the bilayer structure of a sustained release layer and an immediate release layer and containing mosapride as an effective ingredient. The core tablet composite preparation according to the present invention is characterized by exerting sufficient pharmacological activity of rabeprazole and mosapride even upon administration of one tablet once a day.

10 Claims, 7 Drawing Sheets

CORE TABLET COMPOSITE PREPARATION COMPRISING MOSAPRIDE AND RABEPRAZOLE

TECHNICAL FIELD

This application claims priority to and the benefit of Korean Patent Application No. 10-2017-0172473, filed on Dec. 14, 2017, the disclosure of which is incorporated herein by reference in their entirety.

The present invention relates to a combined preparation in a tablet-in-tablet formulation, which is composed of an inner core containing rabeprazole as an active ingredient and an outer layer part containing mosapride as an active ingredient and having a bilayer structure of a sustained-release layer and an immediate-release layer.

BACKGROUND ART

Mosapride, which is a selective serotonin 5-hydroxytryptamine 4 (hereinafter, referred to as "5-HT4") receptor agonist, is a drug that promotes the release of acetylcholine at the nerve end by selectively stimulating only the serotonin 5-HT4 receptors present in the myenteric plexus, in which the acetylcholine contracts the smooth muscle of the digestive tract and promotes digestive tract motility, thereby showing excellent efficacy in the treatment of diabetic gastropathy, dyspepsia, gastritis, and gastroesophageal reflux disease. Mosapride is a safe drug that is free from the risk of arrhythmia or sudden cardiac death caused by the prolongation of the QT interval shown in cisapride which is a non-selective 5-HT4 receptor agonist and has no side effects such as central nervous system (CNS) side effects (extrapyramidal symptoms), hyperprolactinemia (lactation, gynecomastia), or the like without dopamine-2 (D-2) receptor antagonism.

Meanwhile, rabeprazole, which is a benzimidazole derivative, is a drug that inhibits gastric acid secretion and is known as a proton pump inhibitor (PPI) that inhibits gastric acid secretion by inhibiting $H^+/K^+$ ATPase on the surface of the parietal cells of the gastric mucosa for acid secretion. Furthermore, rabeprazole induces inhibition of basal acid secretion and acid secretion by stimulation and is thus attracting attention as a therapeutic agent for peptic ulcers, duodenal ulcers, and the like.

Although combined preparations of the two components having similar drug efficacy have advantages in that they can replace combination therapies, improve a patient's medication convenience, and can be more economical than administering each agent in combination, there is a concern that a change in dissolution pattern or side effects in the body may occur due to an interaction between drugs.

Meanwhile, various formulations for a mosapride and rabeprazole combined preparation are proposed in Korean Laid-open Patent Application No. 2016-0080449, but there is much to be studied on the specific and detailed composition and dosage form of a tablet-in-tablet combined preparation including rabeprazole as an inner core and a mosapride sustained-release preparation as an outer layer part for improving bioavailability.

DISCLOSURE

Technical Problem

The present invention is directed to providing a tablet-in-tablet combined preparation which overcomes the drawbacks of the conventional art related to rabeprazole and mosapride combined preparations and improves bioavailability and medication convenience, and the tablet-in-tablet combined preparation according to the present invention has the same effect as administering a single rabeprazole tablet once and a single mosapride immediate-release tablet three times by only one oral administration of a single tablet a day.

Technical Solution

One aspect of the present invention provides a tablet-in-tablet combined preparation composed of: an inner core containing rabeprazole or a pharmaceutically acceptable salt thereof as an active ingredient; and an outer layer part containing mosapride or a pharmaceutically acceptable salt thereof as an active ingredient, wherein an entire surface of the inner core is surrounded by the outer layer part.

In addition, the outer layer part has a bilayer structure of an immediate-release layer containing an active ingredient, a filler, a disintegrant, and an additive and a sustained-release layer containing an active ingredient, a filler, a disintegrant, a release-modifying agent, and an additive.

Due to the inner core containing rabeprazole as an active ingredient and the outer layer part having a bilayer structure of an immediate-release layer and a sustained-release layer and containing mosapride as an active ingredient, the tablet-in-tablet combined preparation according to the present invention has the same effect as generally administering a single mosapride tablet three times a day and a single rabeprazole tablet once by only one oral administration of a single tablet a day.

In this case, a weight ratio of the sustained-release layer and the immediate-release layer of the outer layer part preferably ranges from 1:1.5 to 1:2.5, and the position of the inner core relative to each layer of the outer layer part may vary depending on the weight ratio. Specifically, the inner core is positioned relatively more toward the immediate-release layer side of the outer layer part, so that a better effect of dissolving the active ingredient of the inner core is exhibited, and the stability of the tablet is maintained.

As described above, as the inner core is positioned relatively more toward the immediate-release layer side of the outer layer part, the area of the inner core surface surrounded by the immediate-release layer of the outer layer part is larger than that surrounded by the sustained-release layer of the outer layer part.

When the proportion of the immediate-release layer relative to the sustained-release layer is less than the above-described range, the inner core is not rapidly separated and dissolved, and thus the dissolution may be delayed, and on the other hand, when the proportion is more than the above-described range, the stability of the inner core is decreased in tableting, and thus it is likely that cracks occur during the dissolution.

In the sustained-release layer of the outer layer part, as the release-modifying agent, a mixture of hydroxypropyl methylcellulose having a viscosity of 75,000 to 140,000 mPa·s and hydroxypropyl methylcellulose having a viscosity of 3,000 to 5,600 mPa·s is used, and, with respect to the total weight of the release-modifying agent, 60 to 70 wt % of the hydroxypropyl methylcellulose having a viscosity of 75,000 to 140,000 mPa·s and 30 to 40 wt % of the hydroxypropyl methylcellulose having a viscosity of 3,000 to 5,600 mPa·s are preferably included.

When the composition ratio of the release-modifying agent is out of the above-described range, the dissolution of the active ingredient is excessively delayed, or the active ingredient is excessively released at the early stage, so that a sufficient sustained-release effect is not exhibited.

Each of the immediate-release layer and sustained-release layer of the outer layer part contains mosapride citrate as an active ingredient. In this case, the immediate-release layer preferably contains 4 to 6 mg of the active ingredient, and the sustained-release layer preferably contains 9 to 12 mg of the active ingredient.

When the immediate-release layer contains less than 4 mg of the active ingredient or the sustained-release layer contains less than 9 mg of the active ingredient, the active ingredient is not sufficiently dissolved at the early stage, and thus the pharmacological effects equivalent to that of administration three times a day is not exhibited. On the other hand, when the immediate-release layer contains more than 6 mg of the active ingredient or the sustained-release layer contains more than 12 mg of the active ingredient, the blood concentration of the active ingredient may be excessively increased, and thus side effects such as vomiting, dizziness, and the like may occur.

According to the tablet-in-tablet combined preparation of the present invention, the sustained-release layer of the outer layer part contains, with respect to the total weight of the sustained-release layer, 12 to 16 wt % of mosapride citrate and 20 to 40 wt % of the release-modifying agent. When the release-modifying agent is contained in an amount of less than 20 wt %, sustained release is not sufficiently achieved, and when contained at more than 40 wt %, the dissolution of the active ingredient is excessively delayed, and thus a pharmacological effect is decreased.

Since the tablet-in-tablet combined preparation of the present invention has a structure in which the outer layer part surrounds the inner core, the size of the whole formulation depends on the size of the inner core. Therefore, a total weight of the inner core is preferably 70 mg or less for a patient's medication convenience and 30 mg or more for maintaining the stability of the inner core in tableting, and is more preferably 40 mg to 60 mg. In addition, the inner core may be coated with an enteric coating agent to enhance the bioavailability of rabeprazole.

In addition, a total weight of the tablet-in-tablet combined preparation including the inner core and the outer layer part is preferably 250 mg or more for the stability of the tablet and 350 mg or less for a patient's medication convenience.

The tablet-in-tablet combined preparation of the present invention is prepared by a method including the following steps:

preparing an inner core containing rabeprazole or a pharmaceutically acceptable salt thereof as an active ingredient;

preparing immediate-release layer granules containing mosapride or a pharmaceutically acceptable salt thereof as an active ingredient, a filler, a disintegrant, and an additive and sustained-release layer granules containing mosapride or a pharmaceutically acceptable salt thereof as an active ingredient, a filler, a disintegrant, a release-modifying agent, and an additive;

feeding the immediate-release layer granules into a punch die of a tablet press machine;

adding the inner core to the punch die into which the immediate-release layer granules have been fed;

applying pre-pressure to the punch die to which the inner core has been added;

feeding the sustained-release layer granules into the punch die to which pre-pressure has been applied; and performing tableting while applying main pressure to the punch die into which the sustained-release layer granules have been fed.

When the steps are performed, particularly, in the order of a step of feeding immediate-release layer granules; a step of adding an inner core; a step of applying pre-pressure; a step of feeding sustained-release layer granules; and a step of performing tableting while applying main pressure, the position of the inner core relative to the outer layer part and the stability of the tablet are most preferably exhibited.

In addition, the pre-pressure preferably ranges from 0.5 to 2 $kgf/cm^2$, and the main pressure preferably ranges from 3 to 20 $kgf/cm^2$, and most preferably, 8 to 15 $kgf/cm^2$.

When the pre-pressure does not reach the above-described range, the inner core is not uniformly positioned. When the main pressure is less than 3 $kgf/cm^2$, the hardness of the tablet-in-tablet combined preparation is decreased, and thus the combined preparation may easily disintegrate, and when the main pressure is more than 20 $kgf/cm^2$, cracks may occur due to excessive pressure.

Advantageous Effects

A tablet-in-tablet combined preparation according to the present invention can have the same effect as administering a single rabeprazole tablet once and a single mosapride immediate-release tablet three times by only one oral administration of a single tablet a day.

In addition, the tablet-in-tablet combined preparation of the present invention has a structure in which an inner core containing a proton pump inhibitor (PPI) is surrounded by an outer layer part having a bilayer structure and containing mosapride. This formulation has not been proposed in the prior art, and the size of the tablet is smaller than that of a conventional tablet-in-tablet preparation, resulting in high medication convenience and excellent stability of the formulation.

MODES OF THE INVENTION

A method of preparing a mosapride- and rabeprazole-containing tablet-in-tablet combined preparation for oral administration according to the present invention is as follows.

The preparation method is roughly divided into four steps as described below, but the present invention is not necessarily limited thereto. Step 1 to Step 3 which are independent processes may be performed by varying the sequence.

Step 1: Preparation of a proton pump inhibitor (PPI) portion (rabeprazole sodium) as a core tablet.

Step 2: Preparation of a digestive tract motility promoter portion (mosapride citrate dihydrate) as an immediate-release layer of an outer layer part.

Step 3: Preparation of a digestive tract motility promoter portion (mosapride citrate dihydrate) as a sustained-release layer of an outer layer part.

Step 4: Tableting of the core tablet and mixtures which are prepared in the Step 1 to Step 3 into a tablet in tablet.

Hereinafter, an embodiment of the method of preparing the mosapride- and rabeprazole-containing tablet-in-tablet combined preparation for oral administration according to the present invention will be described in detail.

Step 1: Preparation of PPI Portion (Rabeprazole Sodium) as Inner Core

With respect to the total weight of an inner core (tablet), 15 to 25 wt % of rabeprazole sodium, 5 to 10 wt % of D-mannitol, 25 to 35 wt % of magnesium oxide, and 3 to 7 wt % of low-substituted hydroxypropyl cellulose were mixed, and the mixture was kneaded with an adequate amount of ethanol, granulated, dried in a dryer at 50 to 70° C. so that loss of dry weight (LOD) became 2% or less, and then sized. Afterward, the resultant was mixed with 2 to 5 wt % of crospovidone and an adequate amount of lubricant and tableted. The tablet thus obtained was primarily coated with a film coating agent and secondarily coated with an enteric coating agent. Finally, the resultant was tertiarily coated with a film coating agent to prepare an inner core in the form of a tablet (coated tablet).

The primary film coating is intended to prevent the interaction between rabeprazole sodium which is an active ingredient and the enteric coating agent and prevent long-term moisture exposure. The secondary enteric coating is intended to achieve the effect of the drug by dissolving the inner core in the intestines while having acid resistance because rabeprazole sodium which is a PPI has a problem of stability such as drug decomposition under acidic conditions. The tertiary film coating is intended to prevent the tablet from being damaged and cracked due to tableting pressure applied to a core tablet in the preparation of a tablet in tablet.

Step 2: Preparation of Digestive Tract Motility Promoter Portion (Mosapride Citrate Dihydrate) as Immediate-Release Layer of Outer Layer Part With respect to the total weight of an immediate-release layer of an outer layer part, 2 to 5 wt % of mosapride citrate, 20 to 40 wt % of lactose, 10 to 20 wt % of low-substituted hydroxypropyl cellulose, and an adequate amount of microcrystalline cellulose were mixed, and the mixture was kneaded with 4 to 8 wt % of povidone K-30 dissolved in ethanol as a binder solution, granulated, dried in a fluid bed dryer at 50 to 70° C. so that LOD became 4% or less, and then sized. Afterward, the resultant was mixed with an adequate amount of lubricant to prepare immediate-release layer granules.

Step 3: Preparation of Digestive Tract Motility Promoter Portion (Mosapride Citrate Dihydrate) as Sustained-Release Layer of Outer Layer Part With respect to the total weight of a sustained-release layer of an outer layer part, 12 to 16 wt % of mosapride citrate as a pharmacological active ingredient, 5 to 15 wt % of lactose, 20 to 40 wt % of a release-modifying agent including hydroxypropyl methylcellulose having a viscosity of 75,000 to 140,000 mPa·s and hydroxypropyl methylcellulose having a viscosity of 3,000 to 5,600 mPa·s, and an adequate amount of microcrystalline cellulose were mixed. The mixture was kneaded with 3 to 7 wt % of povidone dissolved in an adequate amount of ethanol as a binder solution, granulated, dried in a fluid bed dryer at 50 to 70° C. so that LOD became 4% or less, and then sized. Afterward, the resultant was mixed with 15 to 20 wt % of low-substituted hydroxypropyl cellulose and an adequate amount of lubricant to prepare sustained-release layer granules.

Step 4: Tableting of Core Tablet and Mixtures which are Prepared in Step 1 to Step 3 into a Tablet in Tablet The core tablet, immediate-release layer mixture, and sustained-release layer mixture which are prepared in the Steps 1 to 3 were processed using a tablet-in-tablet press machine (PR-LT commercially available from PTK Co. Ltd.) to prepare a mosapride- and rabeprazole-containing tablet-in-tablet combined preparation for oral administration.

First, the immediate-release layer mixture prepared in the Step 2 was fed into a punch die of the tablet press machine, then the core tablet prepared in the Step 1 was added thereto, and a pre-pressure of 0.5 to 2 kgf/cm$^2$ was applied. Subsequently, the sustained-release layer mixture prepared in the Step 3 was fed and tableted while applying a main pressure of 3 to 20 kgf/cm$^2$, preferably, 8 to 15 kgf/cm$^2$.

As the above-described method, the mosapride- and rabeprazole-containing tablet-in-tablet combined preparation for oral administration according to the present invention may be prepared by firstly feeding the immediate-release layer mixture of the outer layer part, adding the previously prepared inner core, applying pre-pressure, feeding the sustained-release layer mixture of the outer layer part, and performing tableting while applying main pressure.

A total weight of the tablet-in-tablet combined preparation according to the present invention ranges from 250 to 350 mg, and it is preferable that the total weight thereof is not more than 350 mg to enhance a patient's drug compliance. In addition, when the total weight thereof is less than 250 mg, the stability of the preparation may be decreased, which is not preferred.

Hereinafter, preferred embodiments of the present invention will be described in detail. The following examples describe specific components and specific factors for the implementation according to the present invention, which are provided to help the overall understanding of the present invention, and the present invention is not limited by the examples.

<Experiment 1> Design of Outer Layer Part and Selection of Optimal Composition

Based on the applicant's mosapride sustained-release technology applied to Gastiin CR tab, the research direction was established by roughly predicting the dissolution pattern and the dissolution range at a specific time, which are main quality attributes of the outer layer part of the tablet in tablet.

In the case of Gastiin CR tab (Korean Registered Patent No. 10-1612931) which is a conventional mosapride-containing sustained-release bilayer tablet, 25 to 45 wt % of the total content of the active ingredient was dissolved after 1 hour under dissolution solution conditions of pH 4.0, pH 1.2, and water, 60 to 80% was dissolved after 8 hours, and 85% or more was dissolved after 24 hours.

Based on this, the applicant has conducted studies in consideration of the characteristics, interactions with other active ingredients, and effects of the tablet-in-tablet formulation. As a result, based on the pH 4.0 dissolution solution which is a standard for commercial approval, a composition capable of stably exhibiting a 35 to 45% active ingredient dissolution after 1 hour and a 70 to 80% active ingredient dissolution after 8 hours was deduced.

Through continuous research and repeated experiments, it was possible to grasp the properties of the raw materials affecting the dissolution pattern and to select a range of the factors. In addition, the degree and relationship of the influence on the dissolution pattern of the raw materials according to the range was established.

Finally, a composition was optimized by analyzing the correlation between the properties of the raw material and the dissolution pattern, and the experimental compositions (MS3 to MS8) of the outer layer part considering the interrelationship between the components were deduced and shown in Table 1 below.

TABLE 1

| Classification | | Purpose of Use | Raw material | Comparative Example 1 (MS3) | Comparative Example 2 (MS4) | Example 1 (MS5) | Example 2 (MS6) | Example 3 (MS7) | Comparative Example 3 (MS8) |
|---|---|---|---|---|---|---|---|---|---|
| Outer Layer part | Immediate-release layer | Main ingredient | Mosapride citrate dihydrate | 5.29 | 5.29 | 5.29 | 5.29 | 5.29 | 5.29 |
| | | Excipient | Microcrystalline cellulose 101 | 31.5 | 31.5 | 31.5 | 31.5 | 31.5 | 31.5 |
| | | Excipient | Lactose hydrate | 32.51 | 32.51 | 32.51 | 32.51 | 32.51 | 32.51 |
| | | Binder | Povidone K30 | 6.7 | 6.7 | 6.7 | 6.7 | 6.7 | 6.7 |
| | | Disintegrant | Low-substituted hydroxypropyl cellulose | 20.0 | 20.0 | 20.0 | 20.0 | 20.0 | 20.0 |
| | | Lubricant | Light anhydrous silicic acid | 2.0 | 2.0 | 2.0 | 2.0 | 2.0 | 2.0 |
| | | Lubricant | Magnesium stearate | 2.0 | 2.0 | 2.0 | 2.0 | 2.0 | 2.0 |
| | | Total of immediate-release layer (mg/tablet) | | 100 | 100 | 100 | 100 | 100 | 100 |
| Outer Layer part | Sustained-release layer | Main ingredient | Mosapride citrate dihydrate | 10.58 | 10.58 | 10.58 | 10.58 | 10.58 | 10.58 |
| | | Excipient | Microcrystalline cellulose | 12.0 | 12.0 | 12.0 | 12.0 | 12.0 | 12.0 |
| | | Excipient | Lactose hydrate | 8.8 | 8.8 | 8.8 | 8.8 | 8.8 | 8.8 |
| | | Release-modifying agent | Hypromellose 2910 (viscosity 4,000 mPa · s) | 10.0 | 6.0 | 6.0 | 10.0 | 10.0 | 13.0 |
| | | Release-modifying agent | Hypromellose 2208 (viscosity 100,000 mPa · s) | 12.0 | 16.0 | 12.0 | 15.0 | 18.0 | 17.0 |
| | | Binder | Povidone K30 | 5.0 | 5.0 | 6.0 | 5.0 | 4.0 | 5.0 |
| | | Disintegrant | Low-substituted hydroxypropyl cellulose | 14.0 | 14.0 | 14.0 | 14.0 | 14.0 | 14.0 |
| | | Lubricant | Light anhydrous silicic acid | 2.0 | 2.0 | 2.0 | 2.0 | 2.0 | 2.0 |
| | | Lubricant | Magnesium stearate | 0.62 | 0.62 | 0.62 | 0.62 | 0.62 | 0.62 |
| | | Total of sustained-release layer (mg/tablet) | | 75 | 75 | 72 | 78 | 80 | 83 |
| Total weight of bilayer tablet (mg/tablet) | | | | 175 | 175 | 172 | 178 | 180 | 183 |

Bilayer tablets were prepared according to the compositions of Examples 1 to 3 and Comparative Examples 1 to 3 (Preparation Nos. MS3 to MS8) as shown in Table 1, and dissolution rates were measured in a pH 4.0 dissolution solution. In order to specify the composition that exhibits an optimal dissolution rate, the bilayer tablets were compared with a conventional Gastiin CR tab which is a control, and results are shown in Table 2 and FIG. 3.

TABLE 2

| Classification | Dissolution rate (%) | | | | | | | | | |
|---|---|---|---|---|---|---|---|---|---|---|
| | 15 mins | 30 mins | 60 mins | 90 mins | 120 mins | 180 mins | 300 mins | 480 mins | 720 mins | 1440 mins |
| Comparative Example 1 (MS3) | 32.8 | 38.1 | 41.9 | 46.0 | 50.7 | 56.4 | 67.4 | 76.0 | 84.1 | 88.7 |
| Comparative Example 2 (MS4) | 37.6 | 42.7 | 46.5 | 51.9 | 57.4 | 63.8 | 71.0 | 80.0 | 88.0 | 97.1 |
| Example 1 (MS5) | 19.6 | 24.6 | 32.1 | 34.9 | 40.2 | 47.9 | 58.5 | 70.5 | 81.7 | 100.0 |
| Example 2 (MS6) | 24.2 | 29.1 | 34.8 | 38.5 | 41.8 | 48.8 | 59.1 | 71.1 | 82.6 | 100.0 |
| Example 3 (MS7) | 19.9 | 31.5 | 39.2 | 44.5 | 46.5 | 51.6 | 61.4 | 72.2 | 81.4 | 101.3 |
| Comparative Example 3 (MS8) | 15.1 | 25.4 | 36.4 | 43.0 | 46.6 | 54.5 | 66.5 | 81.8 | 91.5 | 103.9 |
| Control drug (Gastiin CR tab) | 28.6 | 36.8 | 40.9 | 44.6 | 48.1 | 53.9 | 62.5 | 72.3 | 82.8 | 98.5 |

Figure 3:
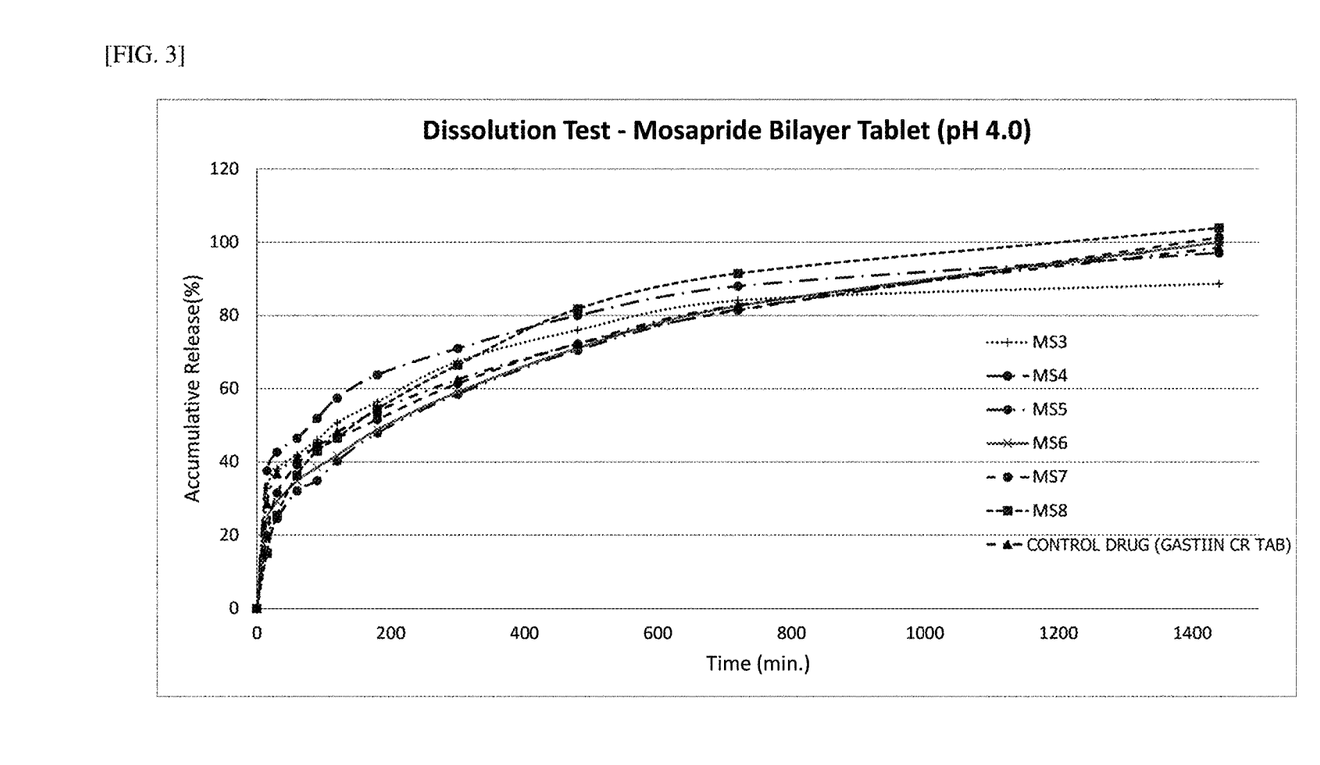
FIG. 3 is a graph illustrating the active ingredient mosapride dissolution rates of bilayer tablets of Examples 1 to 3 and Comparative Examples 1 to 3 which are prepared to specify the composition of an outer layer part of the present invention and a conventional mosapride bilayer tablet which is a control, as measured in a pH 4.0 dissolution solution.

As shown in Table 2 and FIG. 3, Comparative Examples 1 to 3 showed problems such as excessive initial dissolution, long-term delay in dissolution, and the like, whereas Examples 1 to 3 showed preferable dissolution patterns.

Particularly, Example 3 whose dissolution pattern was very similar to that of the control drug was shown to be the most preferable.

<Experiment 2> Design of Inner Core and Selection of Optimal Composition

The mosapride- and rabeprazole-containing tablet-in-tablet combined preparation according to the present invention has a structure in which an inner core, which is a rabeprazole sodium-containing enteric-coated tablet, is surrounded by an outer layer part containing mosapride citrate dihydrate. Therefore, as the weight and size of the inner core tablet increase, the total weight and size of the tablet in tablet increase proportionally thereto, and thereby it is preferable to prepare the core tablet as small as possible in consideration of a patient's medication convenience. However, when the formulation of the core tablet becomes excessively small, cracks may occur in tableting, or stability may be decreased. Considering these conditions, the total weight of the inner core is preferably 30 to 70 mg, and more preferably, 40 to 60 mg.

According to the purpose of the present invention, rabeprazole sodium-containing enteric-coated tablets which maintain stability while having minimized weight (Preparation Nos. RB1 to RB4) were designed as the inner cores, and specific compositions are shown in Table 3 below.

In the preparation of the inner core, a circular punch with a 4π diameter was used.

TABLE 3

| Classification | Purpose of Use | Raw material | Dose (mg/tablet) | | | |
|---|---|---|---|---|---|---|
| | | | Comparative Example 4 (RB1) | Example 4 (RB2) | Comparative Example 5 (RB3) | Example 5 (RB4) |
| Inner core | Active ingredient | Rabeprazole sodium | 10.0 | 10.0 | 10.0 | 10.0 |
| | Excipient | D-mannitol | 4.0 | 4.0 | 4.0 | 4.0 |
| | Stabilizer | Magnesium oxide | 11.0 | 11.0 | 16.0 | 16.0 |
| | Disintegrant | Low-substituted hydroxypropyl cellulose | 3.0 | 3.0 | 3.0 | 3.0 |
| | Disintegrant | Crospovidone | 2.0 | 2.0 | 2.0 | 2.0 |
| | Lubricant | Light anhydrous silicic acid | 3.0 | 3.0 | 3.0 | 3.0 |
| | Lubricant | Sodium stearyl fumarate | 2.0 | 2.0 | 2.0 | 2.0 |
| | | Total of tablet | 35 | 35 | 40 | 40 |
| | Primary film coating agent | Opadry 03K19229 clear | 2.0 | 2.0 | 2.0 | 2.0 |
| | Secondary enteric coating agent | ACRYL-EZE 93A18597 white | 5.0 | 10.0 | 5.0 | 10.0 |

TABLE 3-continued

| | | | Dose (mg/tablet) | | | |
|---|---|---|---|---|---|---|
| Classification | Purpose of Use | Raw material | Comparative Example 4 (RB1) | Example 4 (RB2) | Comparative Example 5 (RB3) | Example 5 (RB4) |
| | Tertiary film coating agent | HPMC 2910 | 2.4 | 2.4 | 2.4 | 2.4 |
| | Tertiary film coating agent | PEG 6000 | 0.6 | 0.6 | 0.6 | 0.6 |
| | Total of enteric-coated tablet | | 45 | 50 | 50 | 55 |

Each preparation shown in Table 3 was measured for the dissolution rate in pH 1.2 and pH 6.8 dissolution solutions which are gastric and intestinal fluid environments, respectively, and results are shown in the following Table 4.

TABLE 4

| | | Dissolution test results (%) | |
|---|---|---|---|
| Classification | Content results (%) test | Dissolution under gastric fluid (buffer solution, pH 1.2) condition for 2 hours | Dissolution under intestinal fluid (buffer solution, pH 6.8) condition for 45 minutes |
| RB1 | 100.9 | 9.4 | 100.8 |
| RB2 | 100.3 | 2.2 | 99.8 |
| RB3 | 101.4 | 9.7 | 101.3 |
| RB4 | 99.9 | 2.3 | 99.7 |
| Control drug (Pariet tab 10 mg) | 100.2 | 2.1 | 100.2 |

As shown in Table 4, among the prepared rabeprazole sodium inner cores, Example 4 (RB2) and Example 5 (RB4) exhibited content and dissolution rate levels equivalent to those of 10 mg of Pariet tab which is a control drug.

Meanwhile, when the weight and size of the tablet are excessively low and small, a punch may be damaged at high tableting pressure due to low tablet thickness, and the tablet may be stuck in a perforated portion inside a coating pan during a coating process. Therefore, in consideration of both the dissolution rate and ease in tableting and coating processes, Example 5 (RB4) was shown to be the most preferable.

<Experiment 3> Preparation of Tablet in Tablet and Selection of Optimal Composition According to Weight Ratio of Each Layer of Outer Layer Part In this experiment, based on the outer layer part composition of Example 3 and the inner core composition of Example 5 which exhibited the most preferable dissolution pattern in Experiment 1 and Experiment 2, additional experiments for ease of separation and dissolution of the inner core were performed. Based on results of the experiments for ease of separation and dissolution, the final preferable composition of the tablet-in-tablet combined preparation according to the present invention was completed.

The outer layer part of the tablet-in-tablet combined preparation according to the present invention is composed of an immediate-release layer that rapidly disintegrates after administration and a sustained-release layer that slowly disintegrates over at least 12 hours, and surrounds the inner core. Therefore, the aspect of the inner core exposed to the external environment varies depending on whether the inner core is positioned more toward the immediate-release layer side or the sustained-release layer side of the outer layer part, and accordingly, the dissolution rate of the active ingredient of the inner core and the stability of the inner core are changed.

As a result of repeated research, the applicants found that it is preferable that the inner core is positioned more toward the immediate-release layer side to ensure the stability of the inner core and achieve the effect of maintaining fast dissolution and high bioavailability.

However, since the inner core is prepared to be positioned close to the center in a conventional method of preparing a tablet in tablet, it is not easy to adjust the position of the inner core itself to be offset from the center, and the process of directly adjusting the inner core is unsuitable for application to tablet tableting equipment for mass production.

Figure 1:
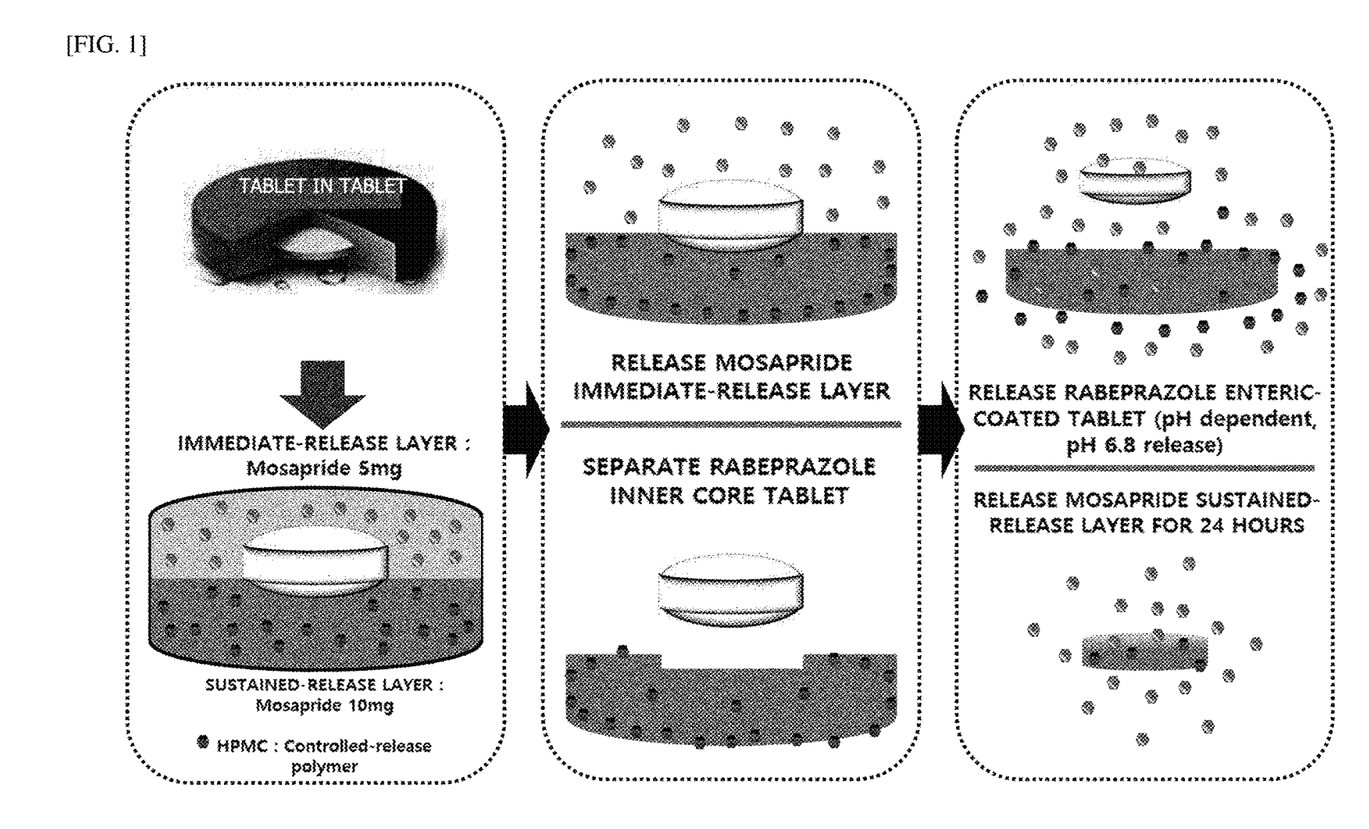
FIG. 1 is a schematic diagram of a tablet-in-tablet preparation according to the present invention.
Figure 2:
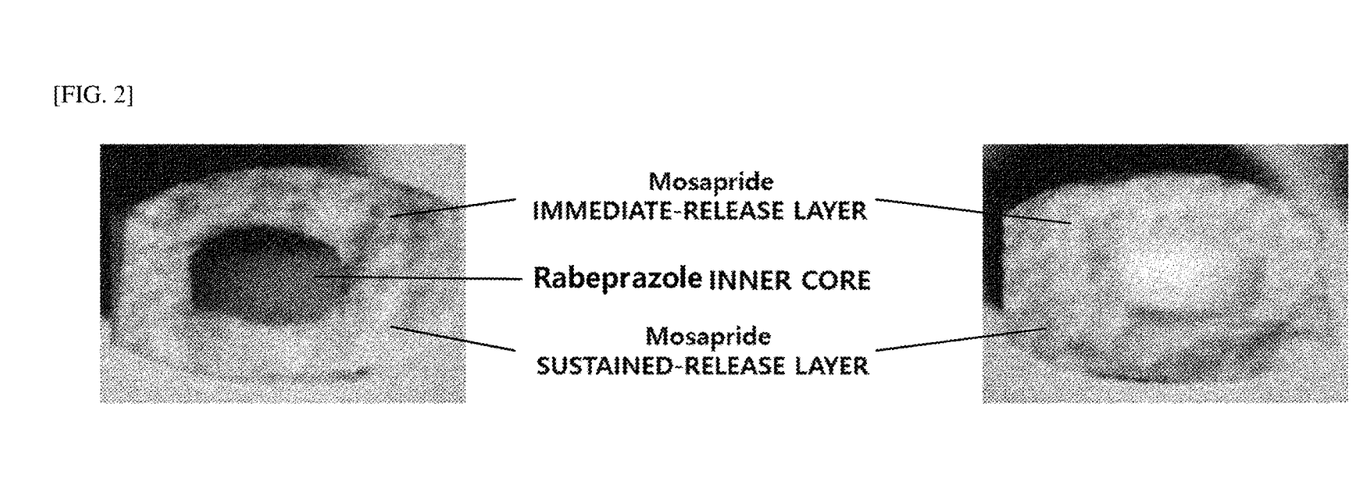
FIG. 2 is an image of the cross-section obtained by longitudinally cutting an outer layer part of a tablet-in-tablet preparation prepared according to the present invention.

Accordingly, as a result of repeated research, the applicants designed a method of adjusting the position of the inner core relative to each layer of the outer layer part by adjusting a thickness ratio of the immediate-release layer and the sustained-release layer of the outer layer part rather than the inner core. Specifically, it was possible to adjust a relative thickness ratio by adjusting the contents of the excipients contained in the immediate-release layer and the sustained-release layer. In addition, when the amount of the excipients was adjusted to increase a weight of the immediate-release layer compared to the sustained-release layer, as shown in FIG. 1 and FIG. 2, the position of the inner core relative to the outer layer part was able to be adjusted to be more toward the immediate-release layer side.

In order to deduce the relative position of the inner core which achieves the most preferable dissolution rate and stability of the inner core, the applicants set various formulations and conducted tableting by varying a preparation method to apply each formulation. Specific compositions (GSP 1 to GSP 9) are shown in Table 5 below, and a circular punch with an 8π diameter was used in the preparation.

Meanwhile, each preparation method listed in Table 5 is as follows.

Preparation method 1: feeding immediate-release layer granules; adding the inner core; applying weak pre-pressure below measurable pressure; feeding sustained-release layer granules; and applying a main pressure of 8.5 kgf/cm².

Preparation method 2: feeding immediate-release layer granules; adding the inner core; applying a pre-pressure of 1 kgf/cm²; feeding sustained-release layer granules; and applying a main pressure of 8.5 kgf/cm².

Preparation method 3: feeding 50 wt % of the prepared immediate-release layer granules; adding the inner core; feeding another 50 wt % of the immediate-release layer granules; applying a pre-pressure of 1 kgf/cm²; feeding sustained-release layer granules; and applying a main pressure of 8.5 kgf/cm².

TABLE 5

| Classification | | Purpose of Use | Raw material | Dose (mg/tablet) | | | | | | | | |
|---|---|---|---|---|---|---|---|---|---|---|---|---|
| | | | | Preparation method 1 | | | Preparation method 2 | | | Preparation method 3 | | |
| | | | | Comparative Example 6 (GSP1) | Comparative Example 7 (GSP2) | Comparative Example 8 (GSP3) | Comparative Example 9 (GSP4) | Example 6 (GSP5) | Example 7 (GSP6) | Comparative Example 10 (GSP7) | Comparative Example 11 (GSP8) | Example 8 (GSP9) |
| Inner core | | Main ingredient | Rabeprazole sodium | 10.0 | 10.0 | 10.0 | 10.0 | 10.0 | 10.0 | 10.0 | 10.0 | 10.0 |
| | | Excipient | D-mannitol | 4.0 | 4.0 | 4.0 | 4.0 | 4.0 | 4.0 | 4.0 | 4.0 | 4.0 |
| | | Stabilizer | Magnesium oxide | 16.0 | 16.0 | 16.0 | 16.0 | 16.0 | 16.0 | 16.0 | 16.0 | 16.0 |
| | | Disintegrant | Low-substituted hydroxypropyl cellulose | 3.0 | 3.0 | 3.0 | 3.0 | 3.0 | 3.0 | 3.0 | 3.0 | 3.0 |
| | | Disintegrant | Crospovidone | 2.0 | 2.0 | 2.0 | 2.0 | 2.0 | 2.0 | 2.0 | 2.0 | 2.0 |
| | | Lubricant | Light anhydrous silicic acid | 3.0 | 3.0 | 3.0 | 3.0 | 3.0 | 3.0 | 3.0 | 3.0 | 3.0 |
| | | Lubricant | Sodium stearyl fumarate | 2.0 | 2.0 | 2.0 | 2.0 | 2.0 | 2.0 | 2.0 | 2.0 | 2.0 |
| | | Primary film coating agent | Opadry 03K19229 clear | 2.0 | 2.0 | 2.0 | 2.0 | 2.0 | 2.0 | 2.0 | 2.0 | 2.0 |
| | | Secondary enteric coating agent | ACRYL-EZE 93A18597 white | 10.0 | 10.0 | 10.0 | 10.0 | 10.0 | 10.0 | 10.0 | 10.0 | 10.0 |
| | | Tertiary film coating agent | HPMC 2910 | 2.4 | 2.4 | 2.4 | 2.4 | 2.4 | 2.4 | 2.4 | 2.4 | 2.4 |
| | | Tertiary film coating agent | PEG 6000 | 0.6 | 0.6 | 0.6 | 0.6 | 0.6 | 0.6 | 0.6 | 0.6 | 0.6 |
| | | Total of inner core (mg/tablet) | | 55 | 55 | 55 | 55 | 55 | 55 | 55 | 55 | 55 |
| Outer layer part | Immediate-release layer | Main ingredient | Mosapride citrate dihydrate | 5.29 | 5.29 | 5.29 | 5.29 | 5.29 | 5.29 | 5.29 | 5.29 | |
| | | Excipient | Microcrystalline cellulose 101 | 13.1 | 48.1 | 63.1 | 13.1 | 48.1 | 63.1 | 13.1 | 48.1 | 63.1 |
| | | Excipient | Lactose hydrate | 43.31 | 43.31 | 43.31 | 43.31 | 43.31 | 43.31 | 43.31 | 43.31 | 43.31 |
| | | Binder | Povidone K30 | 8.3 | 8.3 | 8.3 | 8.3 | 8.3 | 8.3 | 8.3 | 8.3 | 8.3 |
| | | Disintegrant | Low-substituted hydroxypropyl cellulose | 25.0 | 25.0 | 25.0 | 25.0 | 25.0 | 25.0 | 25.0 | 25.0 | 25.0 |
| | | Lubricant | Light anhydrous silicic acid | 2.5 | 2.5 | 2.5 | 2.5 | 2.5 | 2.5 | 2.5 | 2.5 | 2.5 |
| | | Lubricant | Magnesium stearate | 2.5 | 2.5 | 2.5 | 2.5 | 2.5 | 2.5 | 2.5 | 2.5 | 2.5 |
| | | Total of immediate-release layer (mg/tablet) | | 100 | 135 | 150 | 100 | 135 | 150 | 100 | 135 | 150 |
| Outer layer part | Sustained-release layer | Main ingredient | Mosapride citrate dihydrate | 10.58 | 10.58 | 10.58 | 10.58 | 10.58 | 10.58 | 10.58 | 10.58 | 10.58 |
| | | Excipient | Microcrystalline cellulose | 7.0 | 7.0 | 7.0 | 7.0 | 7.0 | 7.0 | 7.0 | 7.0 | 7.0 |
| | | Excipient | Lactose hydrate | 8.8 | 8.8 | 8.8 | 8.8 | 8.8 | 8.8 | 8.8 | 8.8 | 8.8 |
| | | Release-modifying agent | Hypromellose 2910 (viscosity 4,000 mPa·s) | 10.0 | 10.0 | 10.0 | 10.0 | 10.0 | 10.0 | 10.0 | 10.0 | 10.0 |
| | | Release-modifying agent | Hypromellose 2208 (viscosity 100,000 mPa·s) | 18.0 | 18.0 | 18.0 | 18.0 | 18.0 | 18.0 | 18.0 | 18.0 | 18.0 |
| | | Binder | Povidone K30 | 4.0 | 4.0 | 4.0 | 4.0 | 4.0 | 4.0 | 4.0 | 4.0 | 4.0 |
| | | Disintegrant | Low-substituted hydroxypropyl cellulose | 14.0 | 14.0 | 14.0 | 14.0 | 14.0 | 14.0 | 14.0 | 14.0 | 14.0 |

TABLE 5-continued

| | | | Dose (mg/tablet) | | | | | | | | |
|---|---|---|---|---|---|---|---|---|---|---|---|
| | | | Preparation method 1 | | | Preparation method 2 | | | Preparation method 3 | | |
| Classification | Purpose of Use | Raw material | Comparative Example 6 (GSP1) | Comparative Example 7 (GSP2) | Comparative Example 8 (GSP3) | Comparative Example 9 (GSP4) | Example 6 (GSP5) | Example 7 (GSP6) | Comparative Example 10 (GSP7) | Comparative Example 11 (GSP8) | Example 8 (GSP9) |
| | Lubricant | Light anhydrous silicic acid | 2.0 | 2.0 | 2.0 | 2.0 | 2.0 | 2.0 | 2.0 | 2.0 | 2.0 |
| | Lubricant | Magnesium stearate | 0.62 | 0.62 | 0.62 | 0.62 | 0.62 | 0.62 | 0.62 | 0.62 | 0.62 |
| | Total of sustained-release layer (mg/tablet) | | 75 | 75 | 75 | 75 | 75 | 75 | 75 | 75 | 75 |
| Coating | Film coating agent | Opadry 03B28796 white | 5 | 5 | 5 | 5 | 5 | 5 | 5 | 5 | 5 |
| Total weight of tablet in tablet (mg/tablet) | | | 235 | 270 | 285 | 235 | 270 | 285 | 235 | 270 | 285 |

Observation of Presence or Absence of Separation and Disintegration Stability of Inner Core 20 tablets of each of Examples and Comparative Examples prepared according to the compositions and preparation methods shown in Table 5 were prepared, and a paddle was allowed to revolve at 50 rpm/min in a dissolution tester under a pH 1.2 dissolution test solution condition. After 30 minutes of the revolution, the number of tablet in tablets whose core tablet was separated from the mosapride immediate-release layer of the outer layer part and whether the core tablet was cracked were confirmed through visual observation, and results are shown in the following Table 6.

TABLE 6

| Classification | | Weight of immediate-release layer (mg) | Weight of sustained-release layer (mg) | Weight of immediate-release layer (%) | Number of tablets whose core tablet is separated after 30 minutes | Number of core tablets cracked after 30 minutes |
|---|---|---|---|---|---|---|
| Preparation method 1 | Comparative Example 6 (GSP 1) | 100 | 75 | 57.1 | 11 | 1 |
| | Comparative Example 7 (GSP 2) | 135 | 75 | 64.2 | 13 | 0 |
| | Comparative Example 8 (GSP 3) | 150 | 75 | 66.6 | 12 | 0 |
| Preparation method 2 | Comparative Example 9 (GSP 4) | 100 | 75 | 57.1 | 20 | 2 |
| | Example 6 (GSP 5) | 135 | 75 | 64.2 | 20 | 0 |
| | Example 7 (GSP 6) | 150 | 75 | 66.6 | 20 | 0 |
| Preparation method 3 | Comparative Example 10 (GSP 7) | 100 | 75 | 57.1 | 20 | 3 |
| | Comparative Example 11 (GSP 8) | 135 | 75 | 64.2 | 20 | 2 |
| | Example 8 (GSP 9) | 150 | 75 | 66.6 | 20 | 0 |

Discussion

Figure 4:
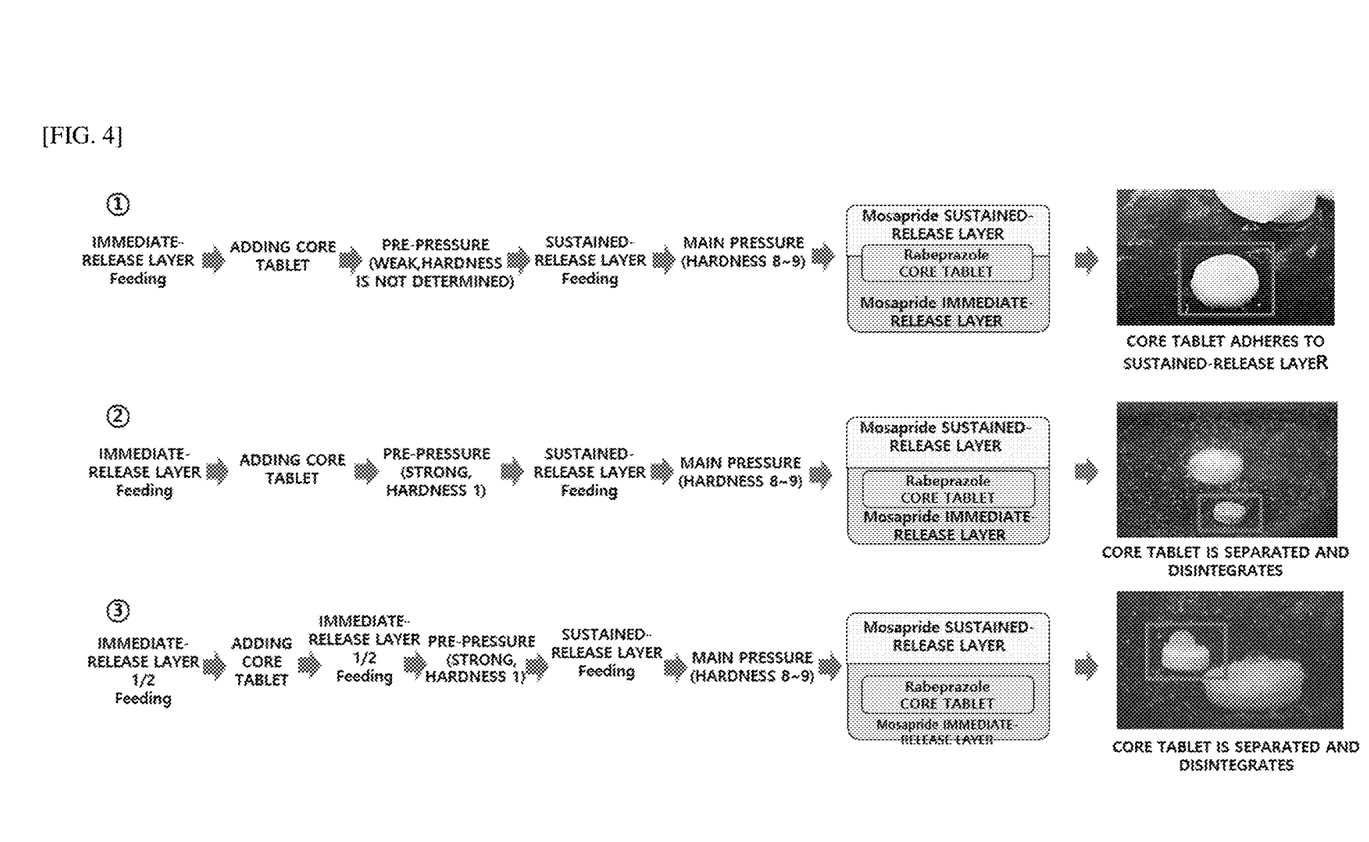
FIG. 4 shows schematic diagrams of tablet-in-tablet combined preparations according to each preparation method and images obtained by photographing whether an inner core is separated in an example.
Figure 5:
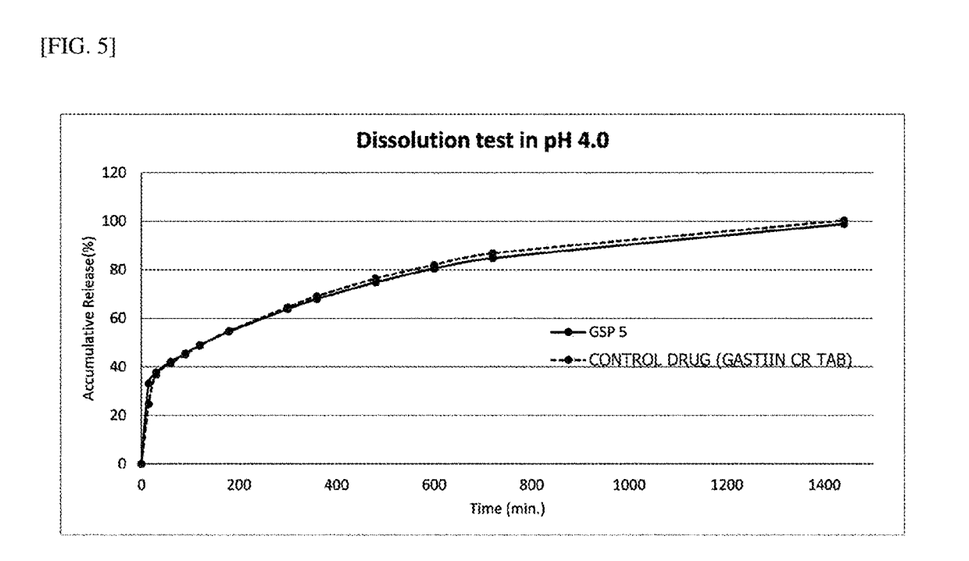
FIG. 5 is a graph of comparing the mosapride dissolution rates of a tablet-in-tablet combined preparation according to Example 6 (GSP 5) of the present invention and Gastiin CR tab, which is a control drug, in a pH 4.0 dissolution solution.
Figure 6:
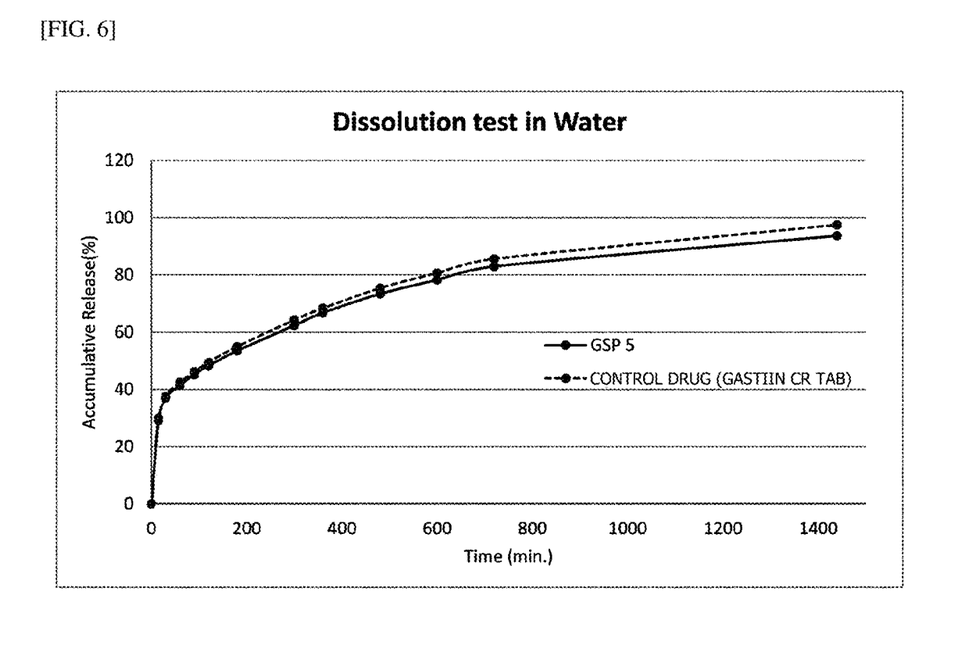
FIG. 6 is a graph of comparing the mosapride dissolution rates of a tablet-in-tablet combined preparation according to Example 6 (GSP 5) of the present invention and Gastiin CR tab, which is a control drug, in water.
Figure 7:
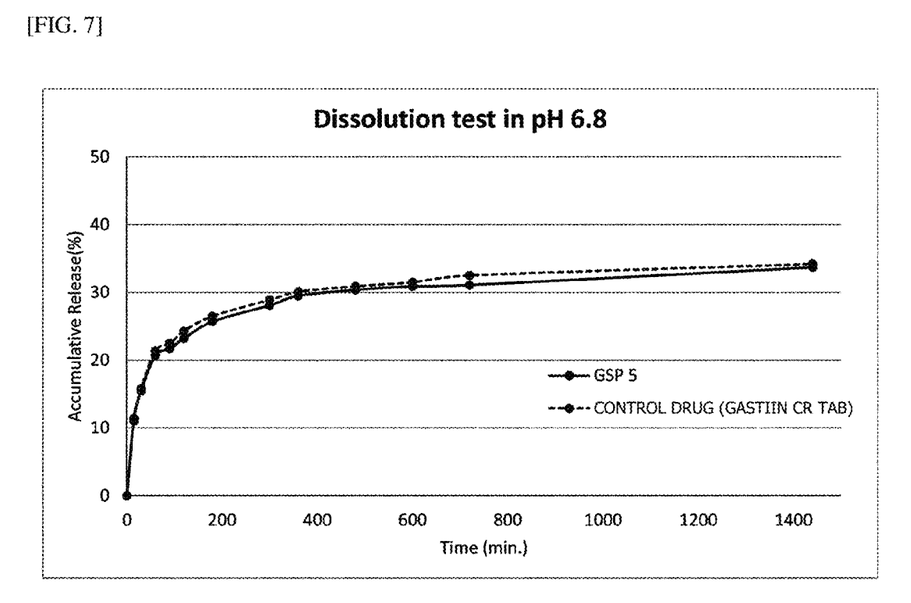
FIG. 7 is a graph of comparing the mosapride dissolution rates of a tablet-in-tablet combined preparation according to Example 6 (GSP 5) of the present invention and Gastiin CR tab, which is a control drug, in a pH 6.8 dissolution solution.
Figure 8:
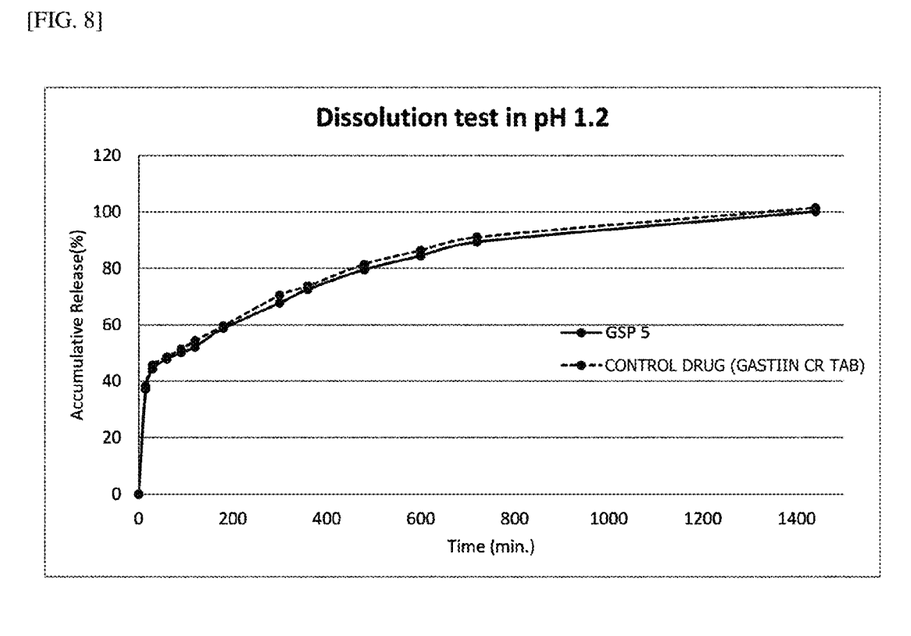
FIG. 8 is a graph of comparing the mosapride dissolution rates of a tablet-in-tablet combined preparation according to Example 6 (GSP 5) of the present invention and Gastiin CR tab, which is a control drug, in a pH 1.2 dissolution solution.

Schematic diagrams of preparation examples and images of separation results according to a preparation method are shown in FIG. 4. In the case of GSP 1 to GSP 3 which were prepared by Preparation Method 1, 100% separation and disintegration of the core tablet did not occur after 30 minutes, and thus it was difficult to exhibit the dissolution pattern expected for the rabeprazole sodium enteric-coated tablet. In the case of GSP 4 to GSP 6 which were prepared by Preparation Method 2, all of the tested 20 tablets showed that the core tablet was separated from the immediate-release layer of the outer layer part and disintegrated. In the case of GSP 7 to GSP 9 which were prepared by Preparation Method 3, all of the tested 20 tablets showed that the core tablet was separated from the immediate-release layer of the outer layer part and disintegrated.

In addition, in the case of GSP 7 and GSP 8 which were prepared by Preparation Method 3 and GSP 1 and GSP 4 which included a low proportion of the immediate-release layer relative to the outer layer part, it is judged that the core tablet is cracked due to the pressure applied during tableting of the tablet in tablet. Since the occurrence of cracks weakens acid resistance of the core tablet, they are unsuitable.

Taken together, GSP 5 (Example 6) prepared by Preparation Method 2 is shown to have the most preferable separability, disintegrability and inner core stability.

<Experiment 4> Experiment for Comparing Active Ingredient Mosapride Dissolution of Outer Layer Part and Control An experiment for comparing dissolution was performed to confirm whether the mosapride-containing outer layer part of the GSP 5 (Example 6) formulation exhibits the same dissolution pattern as a conventional sustained-release tablet.

In-Vitro Dissolution Test for Active Ingredient Mosapride

Under dissolution test solution conditions in the Korean Pharmacopoeia, an active ingredient mosapride citrate dissolution rate of the mosapride- and rabeprazole-containing tablet-in-tablet combined preparation for oral administration according to GSP 5 (Example 6) was measured over time, and a dissolution pattern was confirmed.

Detailed conditions used in the dissolution test are as follows.

Subject: GSP 5 (mosapride- and rabeprazole-containing tablet-in-tablet combined preparation for oral administration)

Dissolution test solution: pH 1.2, pH 4.0, pH 6.8, and water according to the dissolution test method in the Korean Pharmacopoeia Volume of dissolution solution: 900 ml, Test temperature: 37±0.5° C.

Test method: The dissolution test method II (paddle method) in the Korean Pharmacopoeia (50 revolutions/min)

Sample collection: 10 mL of a dissolution solution was taken and filtered through a 0.45-μm filter to obtain a test liquid at each sampling time, and, after taking the dissolution solution, the same amount of a fresh dissolution solution was added.

Analysis equipment: HPLC

Test Results

The in-vitro dissolution test results are shown in the following Tables 7 to 10 and FIGS. 5 to 8.

TABLE 7

Dissolution rate at pH 4.0

Dissolution rate (%) of mosapride citrate

| Classification | 15 mins | 30 mins | 60 mins | 90 mins | 120 mins | 180 mins | 300 mins | 360 mins | 480 mins | 600 mins | 720 mins | 1440 mins |
|---|---|---|---|---|---|---|---|---|---|---|---|---|
| Example 6 (GSP 5) | 33.1 | 37.7 | 42 | 45.5 | 48.9 | 54.5 | 63.8 | 68 | 74.8 | 80.5 | 84.8 | 98.9 |
| Control drug (Gastiin CR tab) | 24.7 | 36.7 | 41.4 | 45.1 | 48.7 | 54.8 | 64.6 | 69.1 | 76.4 | 82 | 86.8 | 100.3 |

TABLE 8

Dissolution rate in water

Dissolution rate (%) of mosapride citrate

| Classification | 15 mins | 30 mins | 60 mins | 90 mins | 120 mins | 180 mins | 300 mins | 360 mins | 480 mins | 600 mins | 720 mins | 1440 mins |
|---|---|---|---|---|---|---|---|---|---|---|---|---|
| Example 6 (GSP 5) | 29.8 | 37 | 41.5 | 45.2 | 48.3 | 53.5 | 62.4 | 66.8 | 73.4 | 78.3 | 83 | 93.7 |
| Control drug (Gastiin CR tab) | 29.1 | 37.5 | 42.5 | 46.2 | 49.5 | 55 | 64.3 | 68.4 | 75.4 | 80.7 | 85.6 | 97.5 |

TABLE 9

Dissolution rate at pH 6.8

Dissolution rate (%) of mosapride citrate

| Classification | 15 mins | 30 mins | 60 mins | 90 mins | 120 mins | 180 mins | 300 mins | 360 mins | 480 mins | 600 mins | 720 mins | 1440 mins |
|---|---|---|---|---|---|---|---|---|---|---|---|---|
| Example 6 (GSP 5) | 11.4 | 15.5 | 20.7 | 21.7 | 23.2 | 25.7 | 28.1 | 29.5 | 30.4 | 30.9 | 31.1 | 33.7 |
| Control drug (Gastiin CR tab) | 11 | 15.8 | 21.4 | 22.5 | 24.3 | 26.5 | 28.9 | 30.1 | 30.9 | 31.5 | 32.5 | 34.2 |

TABLE 10

Dissolution rate at pH 1.2

Dissolution rate (%) of mosapride citrate

| Classification | 15 mins | 30 mins | 60 mins | 90 mins | 120 mins | 180 mins | 300 mins | 360 mins | 480 mins | 600 mins | 720 mins | 1440 mins |
|---|---|---|---|---|---|---|---|---|---|---|---|---|
| Example 6 (GSP 5) | 37.1 | 44.4 | 47.7 | 50.1 | 52 | 58.7 | 67.8 | 72.6 | 79.6 | 84.5 | 89.4 | 100.2 |
| Control drug (Gastiin CR tab) | 38.3 | 45.6 | 48.5 | 51.3 | 54.2 | 59.6 | 70.5 | 73.8 | 81.5 | 86.4 | 91.1 | 101.5 |

Discussion

As shown in Tables 7 to 10 and FIGS. 5 to 8, an active ingredient mosapride citrate dissolution rate of the GSP 5 (Example 6) exhibits the same dissolution pattern as Gastiin CR tab which is a control drug, and thus it can be seen that the GSP 5 is suitable for a preparation for oral administration once a day.

<Experiment 5> Experiment for Comparing Active Ingredient Rabeprazole Dissolution of Inner Core and Control An experiment for comparing dissolution was performed to confirm whether the rabeprazole-containing inner core of the GSP 5 (Example 6) formulation exhibits the same dissolution pattern as a conventional rabeprazole enteric-coated tablet.

In-Vitro Dissolution Test for Active Ingredient Rabeprazole Sodium

Under a pH 6.8 dissolution test solution condition in the Korean Pharmacopoeia, an active ingredient rabeprazole sodium dissolution rate of the mosapride- and rabeprazole-containing tablet-in-tablet combined preparation for oral administration according to GSP 5 was measured over time, and a dissolution pattern was confirmed.

Detailed conditions used in the dissolution test are as follows.

Subject: GSP 5 (mosapride- and rabeprazole-containing tablet-in-tablet combined preparation for oral administration)

Dissolution test solution: pH 6.8 according to the dissolution test method in the Korean Pharmacopoeia Volume of dissolution solution: 900 ml, Test temperature: 37±0.5° C.

Test method: The dissolution test method II (paddle method) in the Korean Pharmacopoeia (50 revolutions/min)

Sample collection: 5 mL of a dissolution solution was taken and filtered through a 0.45-μm filter to obtain a test liquid at each sampling time.

Analysis equipment: HPLC

Test Results

The in-vitro dissolution test results are shown in the following Table 11 and FIG. 9.

TABLE 11

Dissolution rate at pH 6.8

Dissolution rate (%) of rabeprazole sodium

| Classification | 5 mins | 10 mins | 20 mins | 30 mins | 45 mins |
|---|---|---|---|---|---|
| Example 6 (GSP 5) | 0 | 2.4 | 34.2 | 99.8 | 101.2 |
| Control drug (Pariet tab 10 mg) | 0 | 0 | 28.4 | 97.1 | 100.1 |

Discussion

Figure 9:
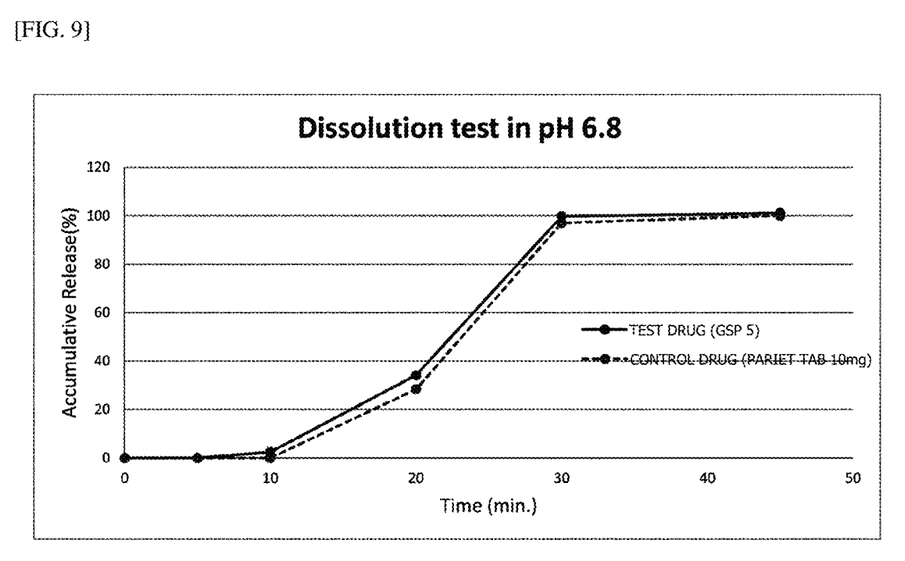
FIG. 9 is a graph of comparing the rabeprazole dissolution rates of a tablet-in-tablet combined preparation according to Example 6 (GSP 5) of the present invention and Pariet tab, which is a control drug, in a pH 6.8 dissolution solution.

As shown in Table 11 and FIG. 9, an active ingredient rabeprazole sodium of the GSP 5 (Example 6) exhibits the same dissolution pattern as Pariet tab, which is a control drug, even though being contained in the inner core of the tablet-in-tablet formulation, and thus the GSP 5 is expected to have optimal bioavailability.

In conclusion, due to the optimal composition and formulation design, the tablet-in-tablet combined preparation according to the present invention exhibits effects of both the active ingredient of the inner core and the active ingredient of the outer layer part by only one oral administration of a single tablet a day.

What is claimed is:

1. A mosapride- and rabeprazole-containing tablet-in-tablet combined preparation for oral administration, the tablet-in-tablet combined preparation composed of:
   an inner core containing rabeprazole or a pharmaceutically acceptable salt thereof as an active ingredient; and
   an outer layer part containing mosapride or a pharmaceutically acceptable salt thereof as an active ingredient,
   wherein an entire surface of the inner core is surrounded by the outer layer part, and
   the outer layer part has a bilayer structure of an immediate-release layer containing an active ingredient, a filler, a disintegrant, and an additive and a sustained-release layer containing an active ingredient, a filler, a disintegrant, a release-modifying agent, and an additive,
   wherein the inner core is positioned more toward an immediate-release layer side of the outer layer part, and
   wherein an area of the inner core surface surrounded by the immediate-release layer of the outer layer part is larger than an area of the inner core surface surrounded by the sustained-release layer of the outer layer part.

2. The tablet-in-tablet combined preparation of claim 1, wherein a weight ratio of the sustained-release layer and the immediate-release layer of the outer layer part ranges from 1:1.5 to 1:2.5.

3. The tablet-in-tablet combined preparation of claim 1, wherein, as the release-modifying agent, a mixture of hydroxypropyl methylcellulose having a viscosity of 75,000 to 140,000 mPa·s and hydroxypropyl methylcellulose having a viscosity of 3,000 to 5,600 mPa·s is used, and, with respect to a total weight of the release-modifying agent, 60 to 70 wt % of the hydroxypropyl methylcellulose having a viscosity of 75,000 to 140,000 mPa·s and 30 to 40 wt % of the hydroxypropyl methylcellulose having a viscosity of 3,000 to 5,600 mPa·s are included.

4. The tablet-in-tablet combined preparation of claim 1, wherein the immediate-release layer of the outer layer part contains 4 to 6 mg of the active ingredient, and the sustained-release layer contains 9 to 12 mg of the active ingredient.

5. The tablet-in-tablet combined preparation of claim 1, wherein the sustained-release layer of the outer layer part contains, with respect to a total weight of the sustained-release layer, 12 to 16 wt % of mosapride citrate and 20 to 40 wt % of the release-modifying agent.

6. The tablet-in-tablet combined preparation of claim 1, wherein a total weight of the inner core ranges from 30 to 70 mg.

7. The tablet-in-tablet combined preparation of claim 1, wherein the inner core is coated with an enteric coating agent, and a total weight of the inner core ranges from 40 to 60 mg.

8. The tablet-in-tablet combined preparation of claim 1, wherein a total weight of the tablet-in-tablet combined preparation ranges from 250 to 350 mg.

9. A method of preparing a mosapride- and rabeprazole-containing tablet-in-tablet combined preparation for oral administration, the method comprising:
  preparing an inner core containing rabeprazole or a pharmaceutically acceptable salt thereof as an active ingredient;
  preparing immediate-release layer granules containing mosapride or a pharmaceutically acceptable salt thereof as an active ingredient, a filler, a disintegrant, and an additive and sustained-release layer granules containing mosapride or a pharmaceutically acceptable salt thereof as an active ingredient, a filler, a disintegrant, a release-modifying agent, and an additive;
  feeding the immediate-release layer granules into a punch die of a tablet press machine;
  adding the inner core to the punch die into which the immediate-release layer granules have been fed;
  applying pre-pressure to the punch die to which the inner core has been added;
  feeding the sustained-release layer granules into the punch die to which pre-pressure has been applied; and
  performing tableting while applying main pressure to the punch die into which the sustained-release layer granules have been fed such that a surface area of the inner core surrounded by the immediate-release layer granules is larger than a surface area of the inner core surrounded by the sustained-release layer granules,
  wherein the inner core is positioned more toward the immediate-release layer granules of an outer layer part.

10. The method of claim 9, wherein the pre-pressure ranges from 0.5 to 2 kgf/cm$^2$, and the main pressure ranges from 3 to 20 kgf/cm$^2$.

* * * * *